United States Patent [19]

Kunke

[11] 4,207,146

[45] Jun. 10, 1980

[54] PROCESS FOR TESTING GASES IN BODY FLUIDS FOR PARTIAL PRESSURE AND TO A TESTING DEVICE THEREFOR

[75] Inventor: Stefan Kunke, Wiesbaden, Fed. Rep. of Germany

[73] Assignee: Drägerwerk Aktiengesellschaft, Fed. Rep. of Germany

[21] Appl. No.: 30,941

[22] Filed: Apr. 17, 1979

Related U.S. Application Data

[63] Continuation-in-part of Ser. No. 866,236, Jan. 3, 1978, abandoned.

[30] Foreign Application Priority Data

Jan. 12, 1977 [DE] Fed. Rep. of Germany ....... 2701020

[51] Int. Cl.$^2$ .......................... G01N 27/46; A62B 7/02
[52] U.S. Cl. .................................. 204/1 T; 128/635; 137/2; 204/195 P; 324/425
[58] Field of Search ................ 204/1 P, 195 P, 195 R; 324/29; 137/2; 128/DIG. 17, 145.8, 145.5, 142 R, 635

[56] References Cited

U.S. PATENT DOCUMENTS

| | | | |
|---|---|---|---|
| 3,493,485 | 2/1970 | MacArthur | 204/1 P |
| 4,042,465 | 8/1977 | Morong et al. | 204/1 T |

OTHER PUBLICATIONS

M. Kogoma et al., Chemical Instrumentation, vol. 7, No. 3, pp. 193-209, (1976).

*Primary Examiner*—G. L. Kaplan
*Attorney, Agent, or Firm*—McGlew and Tuttle

[57] ABSTRACT

A testing device for the partial pressure testing of gases in body fluids comprises a test electrode having a platinum wire extending through a glass tubule arranged in a synthetic tube having a tip with a cellophane layer thereon. The electrode and a counter-electrode are connected through a switch to a pulse generator for generating a control pulse and for also generating a bias voltage pulse. A transverse storage unit is also connected to the switch through a test amplifier. A logic element is connected to the transverse storage for establishing a pulse width, and it is connected through a pulse delay unit and delay circuit. The storage unit is also connected through an amplifier and comparator to a control, warning or indication device. A bias voltage is fed in a pulse to the test electrode, and a test pulse resulting from the current flow of the test electrode is converted to a transfer pulse of a width smaller than that of the test pulse, which is proportional to the amplitude section of the test pulse. The test pulse amplitudinal value is taken over by the transfer pulse and forms the input for a test and/or control circuit.

11 Claims, 6 Drawing Figures

PROCESS FOR TESTING GASES IN BODY FLUIDS FOR PARTIAL PRESSURE AND TO A TESTING DEVICE THEREFOR

BACKGROUND OF THE INVENTION

CROSS-REFERENCE TO RELATED APPLICATION

This is a continuation-in-part of the inventor's co-pending application Ser. No. 866,236 filed Jan. 3, 1978 and now abandoned.

FIELD OF THE INVENTION

The invention relates to a device for the partial pressure testing of gases and in particular to a new and useful device and process for the partial pressure testing of gases in body fluids with an incorporated polarographic test electrode, specifically for the partial pressure testing of oxygen, whereby a bias voltage pulse is applied to the test electrode.

DESCRIPTION OF THE PRIOR ART

On a continual testing of oxygen partial pressure in a person's blood according to the polarographic process various problems are encountered. During testing oxygen is reduced, i.e. consumed at the electrode tip, and with a low blood (or calibration solution) flow rate this results in a slowly dropping tester indication.

To overcome this detrimental "self-consumption of the electrode" there are principally two approaches known, which in any given case also can be applied in combination:

(1) By using a small surface type test electrode, a so-called microelectrode of 5 to 20 microns in tip diameter, the self-consumption of the test electrode and, thus, its conventional function is reduced.

(2) By using relatively thick membranes, which facilitate a slow diffusion of tested gases behind the electrode tip, obstacles to diffusion are produced that continually reduce the self-consumption of the test electrode. If a test electrode having a sufficiently small surface is thickly coated in this way, then usable test values are obtained, where the conventional function is set at about 5% of the test value indication.

Both known processes have substantial drawbacks. The industrial manufacture of a liquid-proof sealed off test electrode, 5 microns in diameter, is very expensive, particularly if the application of an additional covering membrane is required. If for production purposes, however, a mechanically more stable, thicker type of test electrode is to be used (about 100 microns), then to obtain a sufficient degree of convection independence, a very thick coating, partially up to ten layers, must be applied. That way, very long diffusion paths are produced, which cause a high inertia in the test electrode and an extended time drift in measurements.

SUMMARY OF THE INVENTION

The invention provides a process for testing gases in body fluids with an incorporated polarographic test electrode, specifically for the partial pressure testing of oxygen, which uses a simple test electrode design for obtaining a low self-consumption rates high precision and low inertance type of measurement. The test pulse resultant from the test electrode current flow is converted to a transfer pulse proportional to the amplitude of a portion of the test pulse which portion has a narrower width than the test pulse itself. The test pulse amplitude value which is taken for the transfer pulse, constitutes the input for a test and/or control circuit. With this process, the self-consumption of the test electrode and its convectional function can be kept at a minimum without any detrimental effect on the input.

The drawbacks produced in the pulse operation of polarographic electrodes—conditioned by various pulse-shape effecting interference variables—are avoided by selecting a transfer pulse representative of the test pulse interval.

The transfer pulse position and width within the test pulse can be selected in various ways. The transfer pulse however, should not be set or positioned directly in the test pulse rise range because at this location a capacitive type of uncontrolled effect produces a pulse shape deformation. For practical purposes the transfer pulse is set in the test pulse maximum range, namely toward its slowly descending edge or portion.

Because of the low self-consumption of test electrodes used in the outlined process, it is possible to manufacture them in a particularly simple and inexpensive manner. Specifically no diffusion barrier for delaying the gas diffusion is required but only a coarse gating of the test electrode surface against large-size protein molecules. For this purpose, e.g., a thin cellophane protective layer on the electrode surface will do, which will not substantially increase the indicator time lag.

An additional advantage regarding the reduction of test electrode self-consumption is available since the current circuit of the polarographic electrode is high-ohmically interrupted as a function of consumption. Thus during test intervals no discharge of the electrode circuit by the equipment takes place. In this way a favorable, typical time-functional flow of electrode current is obtained.

The measure of control as a function of consumption results in a substantial reduction in self-consumption. The high-ohmic interruption and/or cutoff can be carried out at the point where the test electrode selfconsumption has reached about 1% of its terminal value. This step which is taken in the process is advantageously applicable not only to a transfer pulsing proess but generally to polarographic electrodes which are eneergized with a pulse-like application of bias voltage. On forming a transfer pulse there are specific advantages available, including the practicable option of setting the cutoff point of the electrode current directly after the output of the transfer pulse.

In a further favorable development of the invention the pulse width of the transfer pulse is selected much smaller than that of the test pulse, whereby the pulse width ratio between transfer and test pulses substantially exceeds 1:500.

To be practical also for producing a semi-continual output value a transfer pulse is stored till the arrival of a subsequent transfer pulse.

A favorable circuit engineering solution is that the electrode is connected to an electronic switch, to which a control pulse is fed by a pulse generator. In that way, synchronously with the control pulse, a bias voltage pulse is applied to the test electrode. The output of the electronic switch is fed via a test amplifier to a transfer storage, which is controlled, by switching elements connected therebetween, for establishing pulse width and pulse delay, by the pulse generator derived transfer pulse for its formation, whereby the output value of the transfer storage as an actual value is connected to indicator and/or control and/or regulator devices.

A further practical circuit engineering measure to be taken in this connection is that a cpaacitance is connected between the test electrode and the counter electrode. Such a capacitance, e.g. in the form of an about 500-pF capacitor, is separated (as is the test electrode in a test interval, i.e. after a high-ohmic interruption and/or cutout of test current) from the input circuit of the test device and discharges during the test interval. A subsequent pulse recharges the capacitance, and thus the current flow of the test pulse is effected by a capacitor discharge in the preceding test interval. Thus according to the design of the electrodes the maximal amplitude and slope steepness of the test pulse can be increased. Furthermore, the effect of any unstable self-capacitances present in the circuit can be suppressed. With any given set of electrodes such a capacitance can be used in applicable cases also for an indicator linearization by compensating for any present nonlinearities.

If the indicator characteristic of the test device shows up any nonlinear areas in an undesirable way an additional number of linearization components can be used. Specifically this applies to digital indications, for with analog indications a direct calibration of the indicator unit is carried out.

An application of features according to the invention facilitates a continual testing of blood gases or similar gas components in flowing media by a minimal test processing lag. Continual blood-gas tests such as $O_2$ partial pressure tests can be carried out with an inexpensive catheter electrode, which can be constructed of a disposable material. The pertinent indicator speed is rated 10 times over that of conventional catheter electrodes. Manufacturing costs for the simply designed and mechanically stable test electrodes are low. By comparison with known arrangements, the failure rate of the electronic system is substantially lower, because in the test electrode circuit with short timed if relatively high current flow, an aplification factor can be selected at a relatively low and thus stable rate. Specifically this testing process can be successfully applied to the intensive care of patients.

Accordingly it is an object of the invention to provide a test device for the practical pressure testing of gases in body fluids which includes a test electrode which is connected by an electrical switch to a pulse generator for generating a control pulse and for generating a bias voltage pulse, and is also connected to a transfer storage unit through a test amplifier which further includes logic units connected to the transfer storage for establishing a pulse width and a pulse delay circuit connected to the switch in the logic units, and wherein the transfer storage is connected through a comparator and amplifier to control indicating or warning devices.

A further object of the invention is to provide a process for the partial pressure testing of gases in body fluids with an incorporated polarographic test electrode specifically for oxygen partial pressure testing which comprises feeding a bias voltage in the form of a pulse to the test electrode so that the test pulse resultant from the current flow of the test electrode is converted to a transfer pulse of a width smaller than that of the test pulse, wherein it is proportional to an amplitude section of the test pulse and the test pulse amplitudinal value taken over by the transfer pulse forms the input for a test and/or control circuit.

A further object of the invention is to provide a test device for partial pressure testing of gases in body fluids which is simple in design, rugged in construction, and economical to manufacture.

The various features of novelty which characterize the invention are pointed out with particularity in the claims annexed hereto and forming a part of this disclosure. For a better understanding of this invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
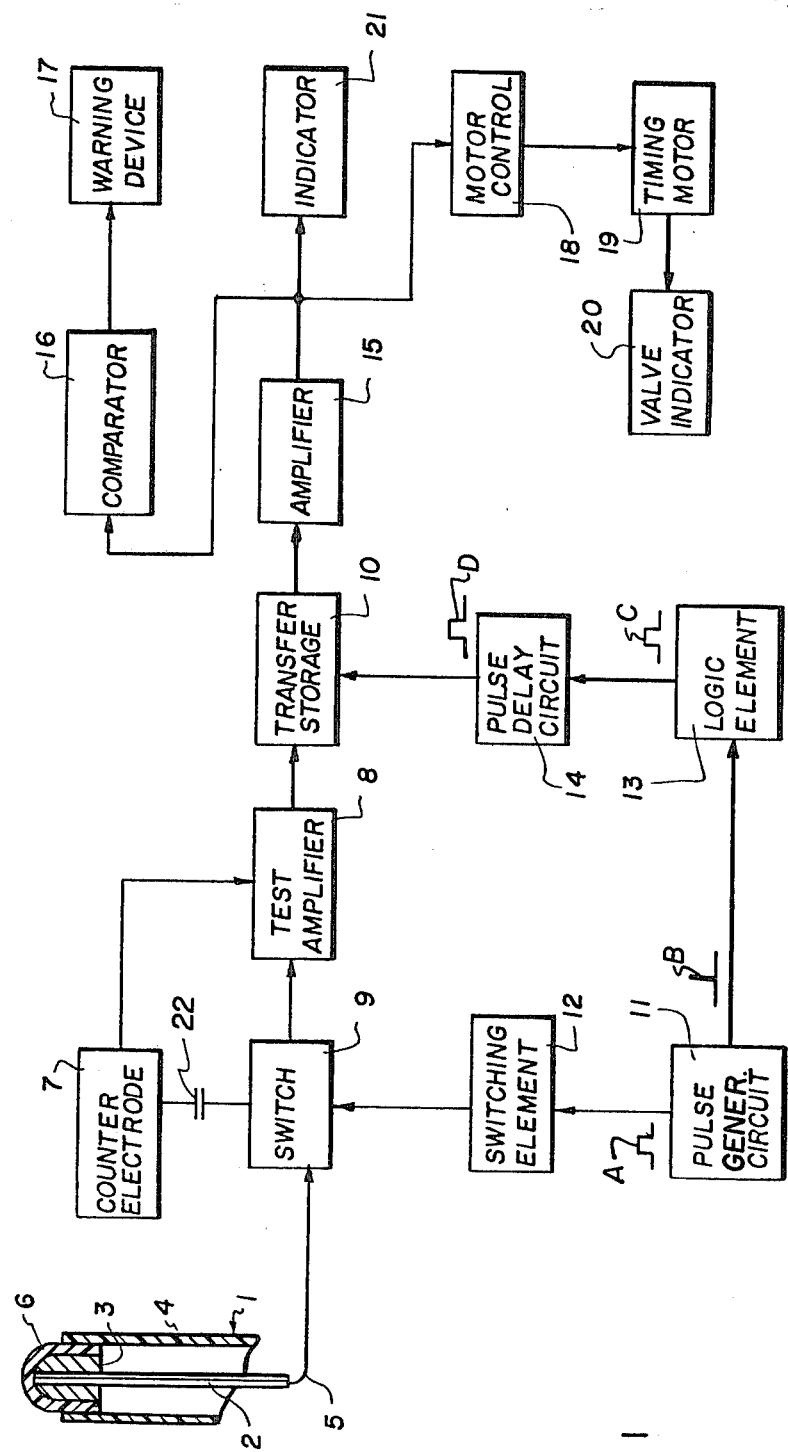
FIG. 1 is a block diagram of a tester constructed in accordance with the invention.

Referring to the drawings in particular, the invention embodied therein in FIG. 1 comprises a text device in the form of a test electrode generally designated 1 and a counter electrode 7 which is connected in a circuit which is schematically indicated by the block diagram for the partial pressure testing of gases in body fluids.

In FIG. 1 a polarographic test electrode 1 consists of a platinum wire 2, 500 microns in diameter, sealed into a glass tubule 3 of about 1 mm in outer diameter. Glass tubule 3 is set in a synthetic material tubular envelope 4, in the internal space of which a line 5 leads to platinum wire 2. The test electrode 1 is screened off with a cellophane layer 6 about 0.2 mm thick or less. It can be inserted into one of the larger vessels via a hollow needle in a simple manner and fixed there. A counter electrode 7, which either is laid onto the skin surface or is additionally built into the test electrode, is single-pole connected to a test amplifier 8. Test electrode 1 equally is single-pole connected to a test amplifier 8 through an electronic switch 9. The output of the test amplifier 8 is fed to a transfer storage unit 10, the output value of which forms the actual value of the quantity to be tested.

The control of electronic switch 9 and transfer storage unit 10 starts from a pulse generator 11, which produces a series of biasing voltage pulses having an adjustable pulse sequence of about 0.1 to 10 seconds. To establish a test pulse width (duration), e.g. of 0.2 ms, the electronic switch 9 is controlled via a timed switching element 12.

To establish a transfer pulse width, e.g. of 10 microseconds, the pulse sequence of pulse generator 11 is further fed to a logic element 13, which is connected to transfer storage unit 10 via a pulse delay circuit 14 that defines the position of the transfer pulse to be positioned within the test pulse, so that from the test pulse a representative transfer pulse is produced.

The actual value output of transfer storage unit 10 is connected to an actual value rated alarm threshold comparator element 16 via an amplifier having a desired-value setting 15. In amplifier 15 the test pulse transferred value of $pO_2=0$ torr (i.e. partial pressure of oxygen is 0 torr) is brought to the indicator value 0 torr by the subtraction of a variable fixed voltage. The actuator required for the desired-value setting is accessible from the outside of the tester for zero-point calibration. On falling below the alarm threshold the actual-value rated alarm threshold comparator element passes a trigger pulse on to an acoustic warning device 17. On falling short of and/or exceeding the desired value settable in amplifier 15 a motor control 18 is activated, via an included comparator, which puts into motion a motor potentiometer and the timing motor 19 of a breathing control valve in a desired direction. The motor and valve comprise means for altering the $O_2$ pressure in the blood. In this case timing motor 19 and motor potentiometer are monitored by valve setting indicator 20. The direct actual valve indication is effected by a digital or analog indicator unit 21. Thus, the output of transfer storage unit 10, which represents the partial pressure of oxygen in the blood tested, is connected to any one or all of various output transducers such as indicator 21, warning device 17 or breathing control 18, 19, 20.

Figure 2A:
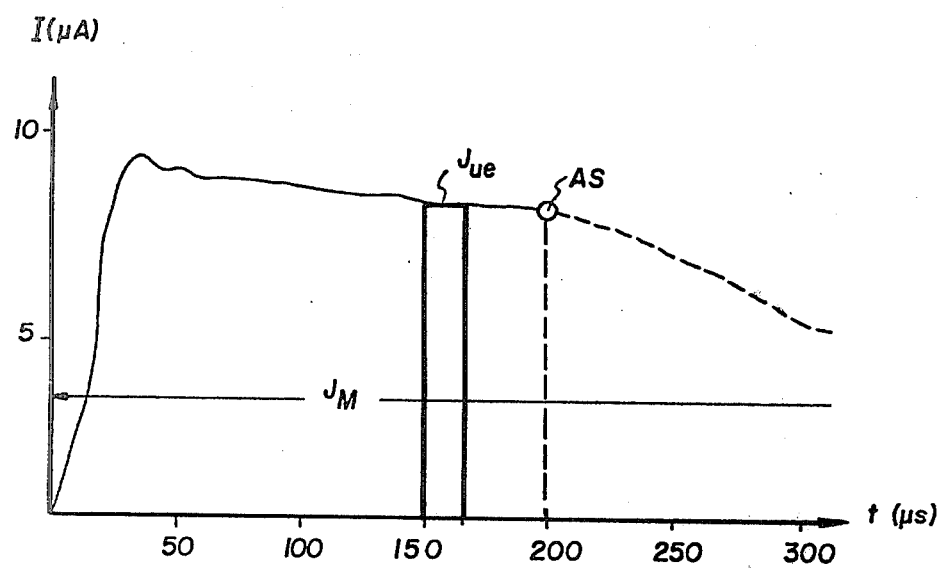
FIGS. 2a and 2b are signal complexes for a tester according to FIG. 1.
Figure 2B:
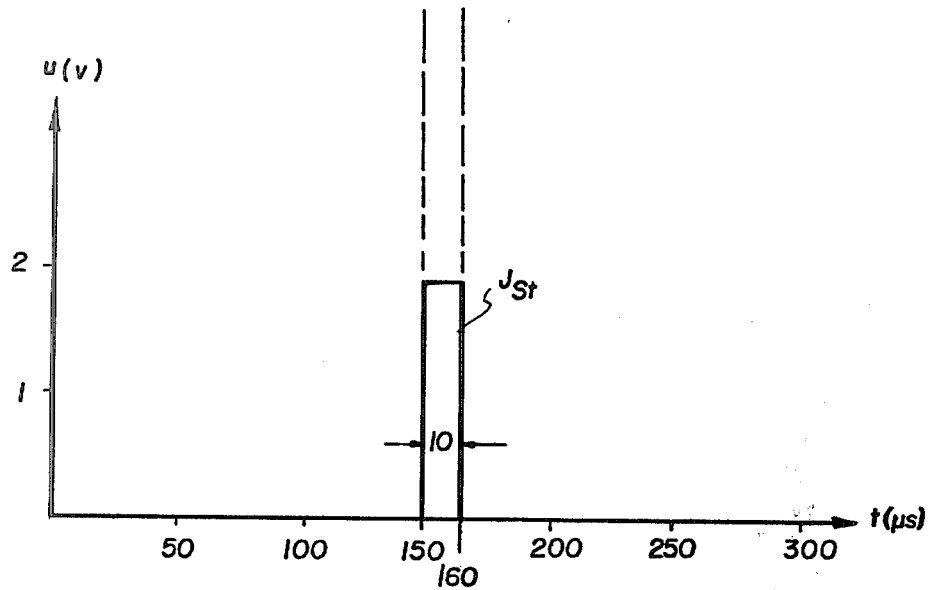

In the circuit, three key pulse magnitudes appear, which are shown in FIG. 2 by way of example.

1. Test pulse $J_M$, resultant from a 500 to 800 mV negative biasing voltage pulse which is applied to test electrode 1, and which with an establised consumption value is cut off at cutoff point AS by electronic switch 9.

2. Transfer control pulse $J_{St}$ (FIG. 2b) which is triggered at about 150 microseconds after the start of the test pulse $J_M$ and has a duration of 10 microseconds.

3. The transfer pulse $J_{ue}$, produced in transfer storage 10 and stored there, which as the transfer control pulse has a 10 microsecond pulse width and selectively reflects and constitutes the amplitudinal value of a test pulse in the 150 microsecond position.

Between test electrode 1 and counter electrode 7 a capacitor 22 is interpolated, which effects the test pulse characteristic flow in any desired manner. The size of this capacitor being a function of electrode design and size in each case is to be determined practicably by experiment.

Figure 3:
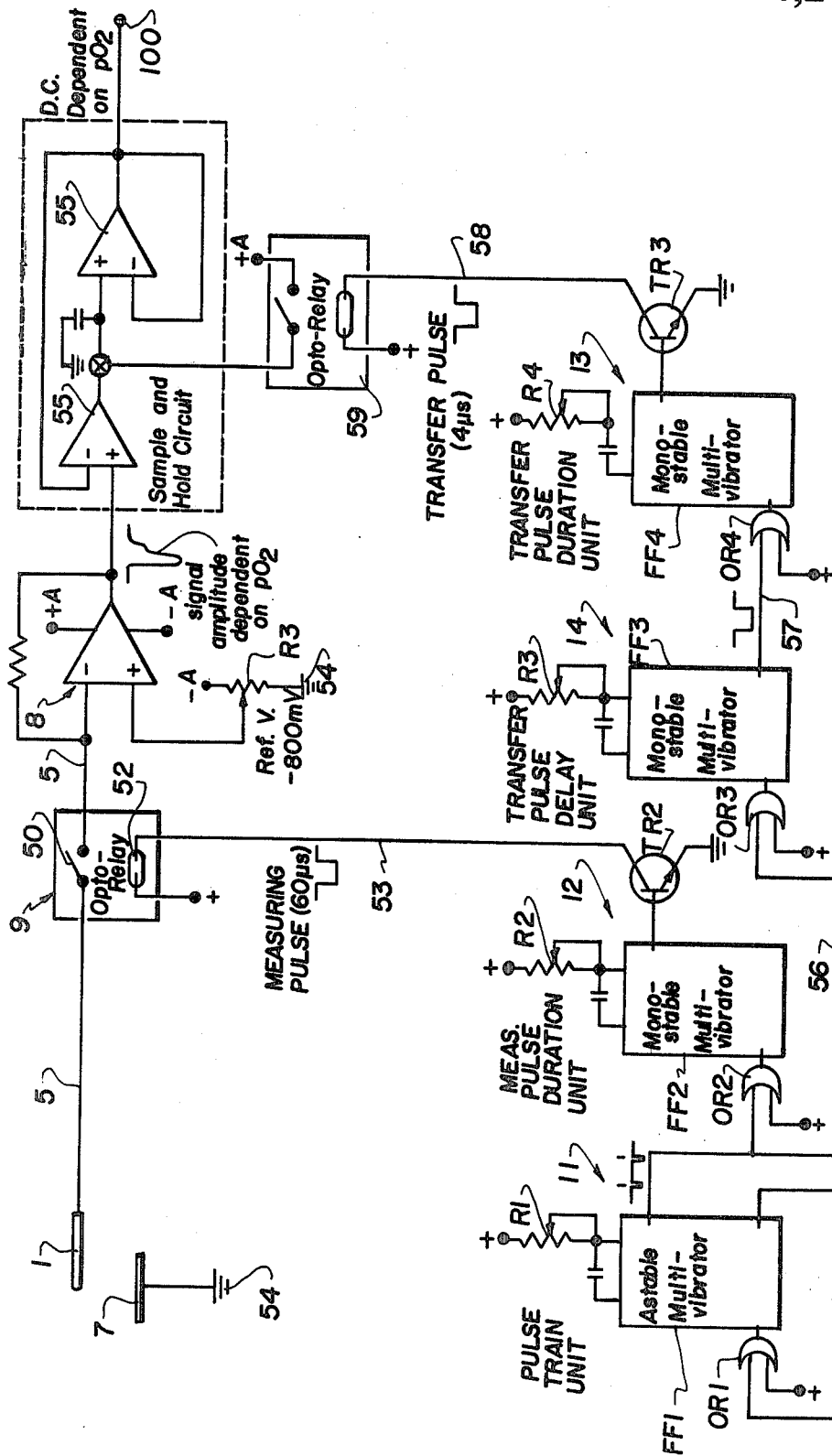
FIG. 3 is a schematic representation of a part of the circuit shown in FIG. 1 indicating specific circuit elements which can be used for practicing the invention.
Figure 4:
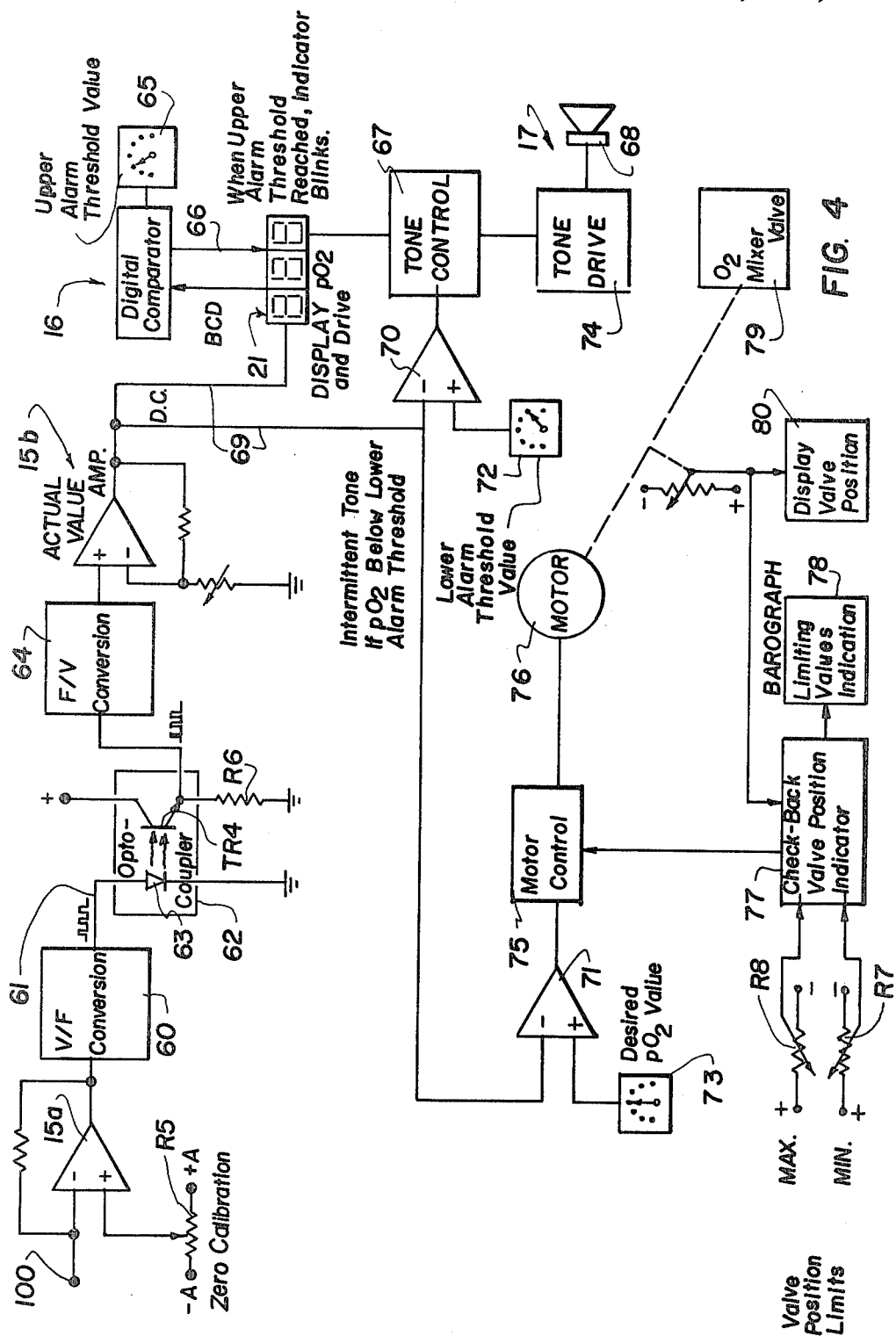
FIG. 4 is a figure similar to FIG. 3 of another part of the circuit shown generally in FIG. 1 which can be interconnected with the circuit of FIG. 3 to complete a preferred embodiment of the invention.

Turning now to FIGS. 3 and 4, specific elements and connections are shown which exemplify the more general block diagram of FIG. 1. Circuit elements which correspond to blocks shown in FIG. 1 are generally designated with the same numeral used in FIG. 1. In the case of amplifier 15 shown in FIG. 1, this single amplifier may be replaced by two separate amplifiers shown as 15a and 15b in FIG. 4. It should be understood that in operation, the circuits of FIGS. 3 and 4 should be connected at their respective terminals 100.

FIG. 3 generally corresponds to the circuit elements shown on the right hand side of FIG. 1 starting from transfer storage 10, pulse delay circuit 14 and logic element 13. FIG. 4 generally corresponds to the circuit elements on the left hand side of FIG. 1 starting with comparator 16 and amplifier 15.

In FIG. 3 electrode 1 with counter electrodes 7 are shown. Electrode 1 is connected to an optical relay switch generally designated 9 which is of conventional design to open and close switch 50 in line 5 depending on whether light source 52 is emitting light or is dark. Light 52 is powered through line 53 by a flip-flop FF2 through a transistor TR2. Flip flop FF2 with transistor TR2 and variable resistor R2 comprise the switching element generally designated 12. Flip flop FF2 is controlled by a pulse trans generator comprising a flip flop FF1 connected at its Q terminal to an OR element OR2. Flip flop FF1 includes an OR element OR1 connected to its input and fed by the output $\bar{Q}$, with variable resistor R1 for varying the duration of pulses generated by FF1. These last mentioned elements act as an astable multivibrator which serves the purpose of the pulse delay circuit 11 of FIG. 1. Test amplifier generally designated 8 is of conventional design and is connected to line 5. It is understood that amplifier 8 is connected to the counter electrode 7 through ground 54 and through a variable resistor R3. For a better understanding of the invention, the pulse configuration in various lines of FIG. 3 are shown adjacent to these lines with labels. A sample and hold circuit generally designated 10 corresponds to the transfer storage of FIG. 1 and comprises tandem amplifiers 55. The delay of the transfer pulse from flip flop FF1 is accomplished in delay element generally designated 14 and comprising flip flop FF3 with OR element OR3 and variable resistor R3. FF1 is connected to FF3 through line 56 and an output $\bar{Q}$ is connected to a duration control element generally designated 13 through a line 57. Duration element 13 comprises flip flop FF4 with OR element OR4 and variable resistor R4 and corresponds to the logic element 13 of FIG. 1. Output Q of FF4 is connected through a transistor TR3 through line 58 to an optical relay 59 which controls the supply voltage for amplifiers 55. In the output of amplifiers 55 is connected to terminal 100 which is common with terminal 100 of FIG. 4. Turning to FIG. 4, a first amplifier 15a is provided with a negative input from terminal 100 and also connected to a "zero calibration": reference voltage through a variable resistor R5. The output of amplifier 15a is fed to a voltage to frequency converter 60 which is of conventional design. Voltage to frequency converter provides a series of pulses in output line 61 which feeds an optical coupler 62 which itself is of conventional design. Optical coupler 62 comprises a light emitting diode 63 which emits light toward a light sensor in the form of transistor TR4. The emitter of transistor TR4 is connected to ground through resistor R6 and feeds the input of a frequency to voltage converter 64 which in turn provides an output to a positive input of amplifier 15b. Amplifier 15b serves as an actual value amplifier for the partial pressure of oxygen and feeds a digital display 21 of conventional design. Digital diplay 21 is connected to a digital comparator 16 which is set for an upper alarm threshold value by a multi position switch 65. Linw 66 is connected between digital display 21 and tone control 67 for producing a continuous tone in a speaker 68 when the display reads "000" indicating a rupture of the electrode membrane. The actual value of the partial pressure of oxygen as generated by amplifier 15b is also fed through line 69 to amplfiers 70 and 71 which respectively have positive inputs connected to multiposition switches 72 and 73 for providing a lower alarm threshold value for the partial pressure of oxygen at switch 72 and a desired value for the partial pressure of oxygen at switch 73. Amplifier 70 is also connected to tone control 67 which in turn is connected to a tone producing element 74 which is connected to the alarm or speaker 68. Tone control 67, tone producer 74 and speaker 68 comprise warning device 17 of FIG. 1. Amplifier 71 energizes motor control 75 when the partial pressure of oxygen sensed is above or below the threshold value defined by switch 73. In this event, motor control 75 operates motor 76 in the forward or reverse direction to increase or decrease the amount of oxygen supplied. Motor control 75 with motor 76 comprise the motor control and timing motor 18 and 19 respectively of FIG. 1. A check back valve position indicator 77 is provided with maximum and minimum values by variable resistors R7 and R8. A limit values indicator 78 is provided for indicating the values set on the check back valve position indicator 77. Motor 76 is mechanically connected to a mixer valve 79 for mixing the oxygen with other gases to be supplied for varying the amount of oxygen supplied. A display value position device 80 is connected to the indicator 77 and cooperates with the limit values indicator 78 to form a barograph.

Figure 5:
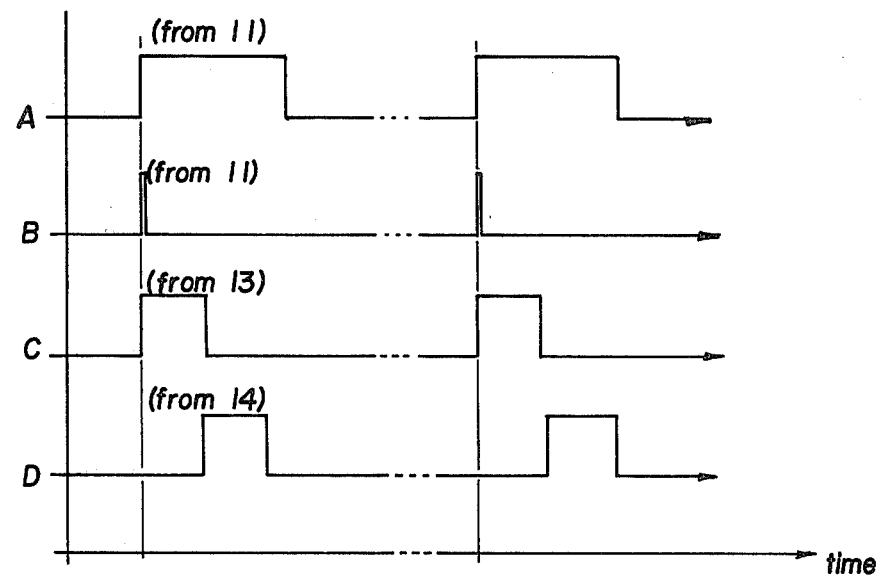
FIG. 5 is a graphic representation of the pulses generated at various labelled locations in the circuit of FIG. 1 which are time correlated with each other to show the respective positions of these pulses.

Turning now to FIG. 5, the pulses labelled at positions A, B, C and D in FIG. 1 are shown in relationship to each other as plotted against time. In FIG. 5 upper case A shows the biasing voltage pulse coming from the pulse generator circuit 11 and B shows the trigger pulse coming from that circuit. C signifies the undelayed transfer control pulse coming from logic element 13 with D showing the transfer control pulse which has been delayed by pulse delay circuit 14.

Thus in accordance with FIGS. 3 and 4 a specific combination of known elements is disclosed for practicing the invention shown generally in FIG. 1.

While specific embodiments of the invention have been shown and described in detail to illustrate the application of the principles of the invention, it will be understood that the invention may be embodied otherwise without departing from such principles.

What is claimed is:

1. A process for the polarographic testing of the partial pressure of oxygen in a body fluid using a pair of electrodes at least one of which is disposed within the body fluid and has a semi-permeable membrane thereon, comprising feeding a biasing voltage pulse to the electrode disposed within the body fluid to form a test pulse resulting in a current flow between the electrodes, forming a transfer control pulse of a duration smaller than the duration of said test pulse and beginning at a time after the beginning of said test pulse and at least when said test pulse has risen to its maximum amplitude, impressing said control transfer pulse on said test pulse to form a transfer pulse having a duration substantially equal to the duration of said transfer control pulse and an amplitude substantially proportional to the amplitude of said test pulse during the time of said transfer control pulse, amplifying said transfer pulse, and applying said amplified transfer pulse to an output transducer, whereby said amplified transfer pulse is proportional to the partial pressure of oxygen in a body fluid and can be utilized to indicate the partial pressure, sound a warning, or actuate means for altering the partial pressure of oxygen in the body fluid.

2. A process according to claim 1, wherein the transfer control pulse is positioned in the area of said test pulse having maximum amplitude.

3. A process according to claim 1, wherein the electrode is a polarographic electrode having high resistance which is a function of its oxygen consumption.

4. A process according to claim 1, wherein the biasing voltage pulse to the electrode ends immediately after the end of said transfer control pulse.

5. A process according to claim 1, wherein the duration of the transfer pulse is about 1:500 by comparison with that of the test pulse.

6. A process according to claim 1, including storing the transfer pulse until the arrival of a subsequent transfer pulse in order to produce a quasi-continual output.

7. A test device for testing the partial pressure of oxygen in body fluids, comprising a test electrode insertable into the body fluids to be tested, said electrode comprising a central wire, and a tubular envelope disposed around and covering said wire made of a material which is permeable to oxygen to be tested and impermeable to the body fluid, a pulse generator (11) connected to said electrode for applying a biasing voltage pulse to said electrode for producing a test pulse, a logic element (13) connected to said pulse generator (11) for producing a transfer control pulse of a duration shorter than the duration of said biasing voltage pulse, a pulse delay circuit (14) connected to said logic element for delaying the start of said transfer control pulse at least until said test pulse has reached a maximum value amplitude, a test amplifier (8) connected to said electrode for amplifying said test pulse, a transfer storage unit (10) connected to said test amplifier and said pulse delay circuit for impressing said transfer control pulse onto said amplified test pulse to produce a transfer pulse having a duration substantially equal to the duration of said transfer control pulse and an amplitude substantially proportional to the amplitude of said test pulse during the time of said transfer control pulse and at least one output transducer connected to said transfer storage unit for receiving said transfer pulse whereby said transfer oukse is proportional to the partial pressure of oxygen in a body fluid.

8. A device according to claim 7, wherein said output transducer comprises at least one of a warning device for producing a warning indication when a partial pressure of the gas in the body fluid to be tested falls below or rises above a predetermined value, an indicator for indicating the partial pressure of the bas in the body fluid to be tested, and means for altering the partial pressure of the gas in the body fluid.

9. A process for the polarographic testing of the partial pressure of a gas in a body fluid using a pair of electrodes at least one of which is disposed within the body fluid, comprising feeding a biasing voltage pulse to the electrode disposed within the body fluid to form a test pulse resulting in a current flow between the electrodes, forming a transfer control pulse of a duration smaller than the duration of said test pulse and beginning at a time after the beginning of said test pulse and at least when said test pulse has risen to its maximum amplitude, impressing said control transfer pulse on said test pulse to form a transfer pulse having a duration substantially equal to the duration of said transfer control pulse and an amplitude substantially proportional to the amplitude of said test pulse during the time of said transfer pulse, amplifying said transfer pulse, and applying said amplified transfer pulse to an output transducer, whereby said amplified transfer pulse is proportional to the partial pressure of a gas in a body fluid and can be utilized tu indicate the partial pressure, sound a warning, or actuate means for altering the partial pressure of a gas in the body fluid.

10. A process according to claim 9, wherein the transfer control pulse is positioned in the area of said test pulse having maximum amplitude.

11. A process according to claim 9, wherein the biasing voltage pulse to the electrode ends immediately after the end of said transfer control pulse.

* * * * *